US00PP36853P2

(12) United States Plant Patent
Johnson, Jr.

(10) Patent No.: US PP36,853 P2
(45) Date of Patent: Jul. 22, 2025

(54) ***BEGONIA* PLANT NAMED 'Neon Moon'**

(50) Latin Name: ***Begonia* hybrid**
Varietal Denomination: Neon Moon

(71) Applicant: Ozzie W. Johnson, Jr., Marietta, GA (US)

(72) Inventor: Ozzie W. Johnson, Jr., Marietta, GA (US)

( * ) Notice: Subject to any disclaimer, the term of this patent is extended or adjusted under 35 U.S.C. 154(b) by 0 days.

(21) Appl. No.: 18/944,068

(22) Filed: Nov. 12, 2024

(51) Int. Cl.
*A01H 6/18* (2018.01)
*A01H 5/02* (2018.01)

(52) U.S. Cl.
USPC ..... Plt./343

(58) Field of Classification Search
USPC ..... Plt./343
CPC ..... A01H 6/185; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Begonia* plant named 'Neon Moon' is disclosed, characterized by its dark green foliage mottled with silver. Plants exhibit a clumping plant form, root hardiness, and large leaf size. Flowers are light pink with darker pink flower buds. The new cultivar is a *Begonia*, typically suited for garden and ornamental container use.

2 Drawing Sheets

Latin name of the genus and species: *Begonia* hybrid.
Cultivar denomination: 'Neon Moon'.

BACKGROUND OF THE INVENTION

The new cultivar is a product of a planned breeding program. The new cultivar originated from an open-pollination of various unnamed, unpatented *Begonia* species and cultivars by the inventor during 2012. The crossing was made in Marietta, GA in the inventor's garden.

'Neon Moon' was selected by the inventor, in 2013 Marietta, GA in the inventor's garden.

After selection of the new cultivar, asexual reproduction of 'Neon Moon' was first performed at the inventor's home by leaf cuttings in 2014. 'Neon Moon' has since produced several generations and has shown that the unique features of this cultivar are stable and reproduced true to type.

SUMMARY OF THE INVENTION

The cultivar 'Neon Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Neon Moon.' These characteristics in combination distinguish 'Neon Moon' as a new and distinct *Begonia* cultivar:

1. Dark green foliage mottled with silver.
2. Root hardiness.
3. Clumping plant form.
4. Light pink flower and darker pink flower buds.
5. Large foliage.

PARENTAL COMPARISON

Exact parentage cannot be identified.

COMMERCIAL COMPARISON

Plants of the new cultivar 'Neon Moon' are similar to the commercial cultivar 'Fireworks', unpatented, in most horticultural characteristics. However, 'Neon Moon' differs in the following:

1. The new cultivar is more root hardy.
2. The new cultivar has a larger flower size
3. Plants of the new cultivar are larger and taller.
4. The new cultivar has more foliage cover over the plant.
5. The new cultivar does not have the maroon marginal coloration found on 'Fireworks'.

Plants of the new cultivar 'Neon Moon' are similar to the commercial cultivar 'Metallic Mist' U.S. Plant Pat. No. 19,567 in most horticultural characteristics. However, 'Neon Moon' differs in the following:

1. The new cultivar has more colorful foliage.
2. The new cultivar is more tolerant of heat and humidity.
3. The new cultivar is more root hardy.
4. The new cultivar has a larger leaf size
5. The new cultivar has a larger flower size
6. Plants of the new cultivar are larger.

BRIEF DESCRIPTION OF THE PHOTOGRAPHS

Figure 1:
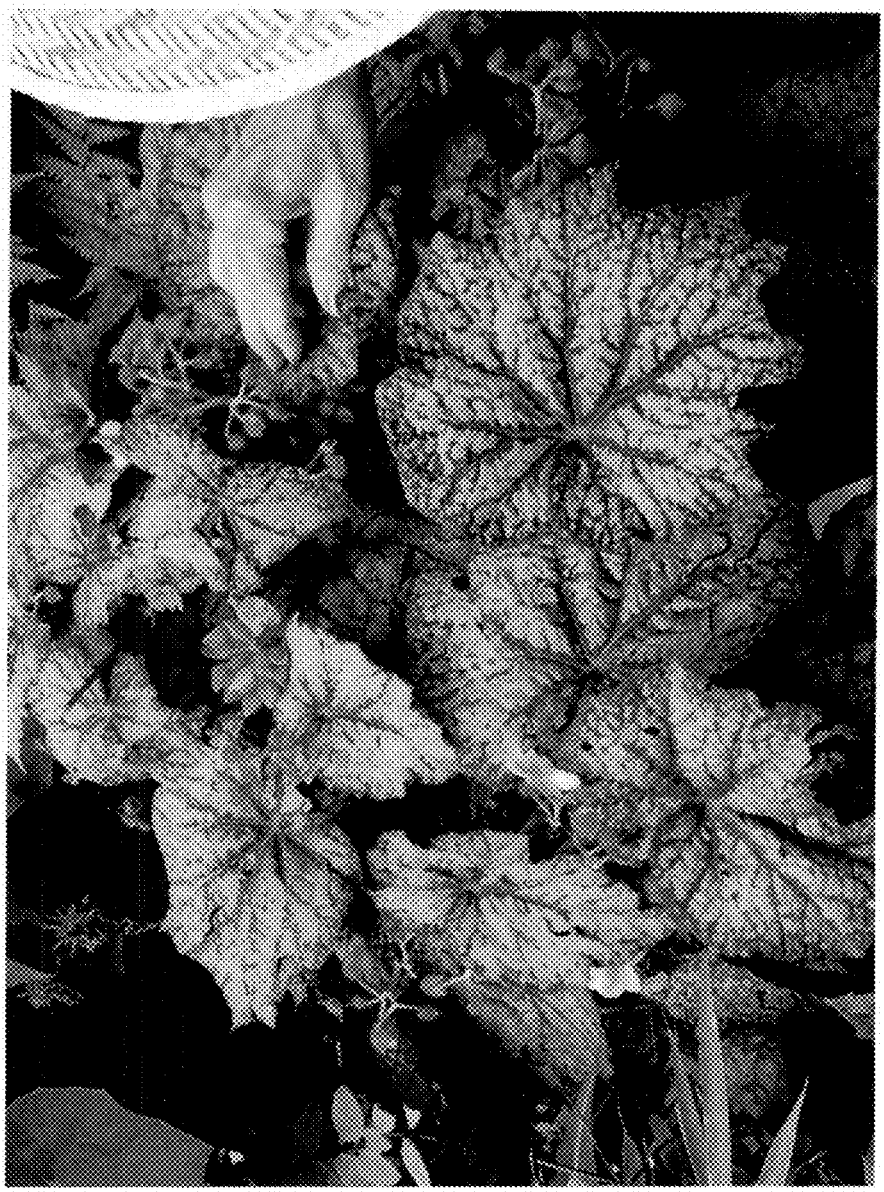

The accompanying photograph in FIG. 1 illustrates in full color a typical plant of 'Neon Moon' grown outdoors in Mobile, Alabama. This plant is approximately 1 year old, planted in a in a shady location in the ground.

Figure 2:
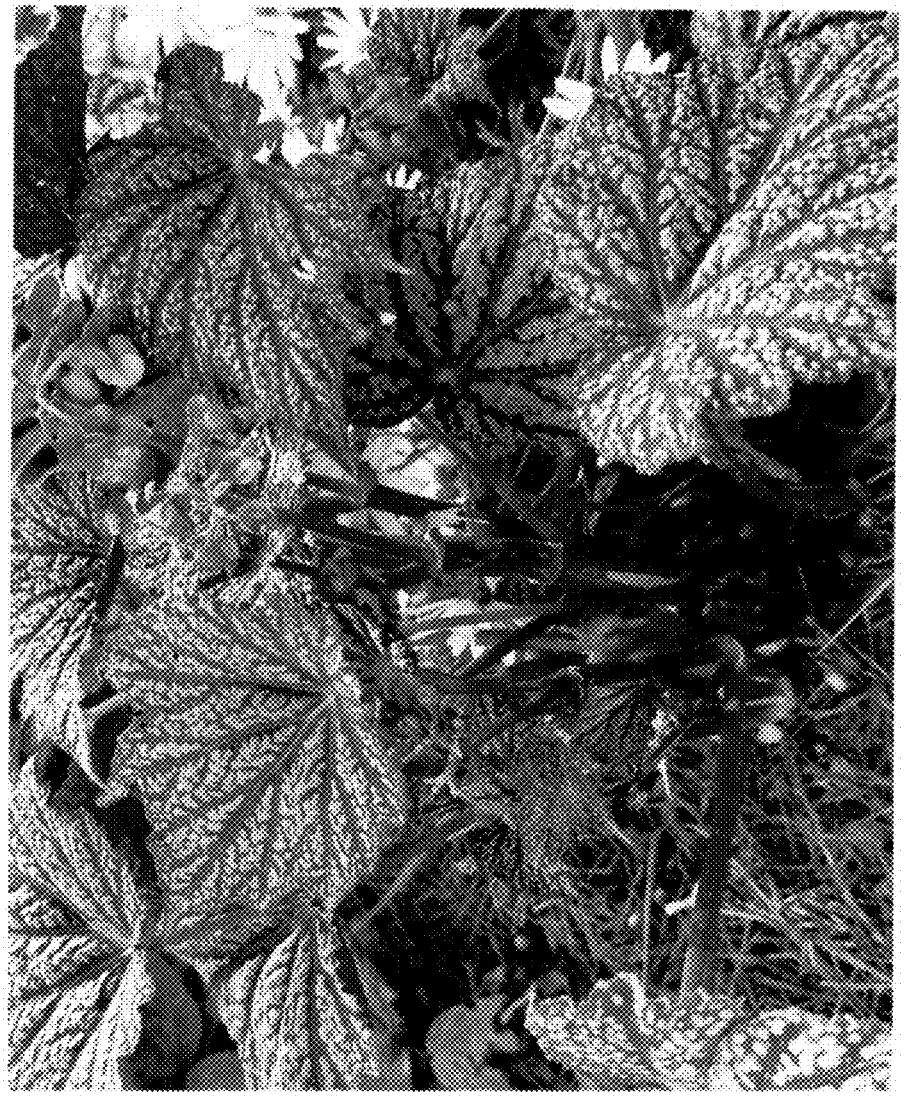

FIG. 2 is a photograph of a different plant of 'Neon Moon' grown in a sunnier location and showing the clumping growth habit. The plant in FIG. 2 is about 10 months old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Neon Moon' plants grown in a shade house in Woodlake, CA during Summer. Temperatures ranged from a low temperature about 55° F. at night to a high around 90° C. during the day. No artificial light, photoperiodic treatments or chemical treatments were given to the plants. Measurements and numerical values represent averages of typical plant types.

Botanical classification: *Begonia* hybrid 'Neon Moon'.

Age of the plant described: Approximately 1 year.

Container size of the plant described: 1-gallon commercial container.

PROPAGATION

Typically reproduced commercially by tissue culture. Leaf cutting propagation is also possible.

PLANT

Growth habit: Upright flowering tender perennial. Clumping, not rhizomatous.

Pot size of plant described: 1-gallon.

Height: Mature plants about 40 to 55 cm.

Plant spread: Mature plants about 45 to 60 cm.

Growth rate: Moderate to rapid.

Branching characteristics: Basal branching, breaking into 2 lateral branches at about 10 cm with maturity.

Quantity of stems/branches: About 15 to 20.

Characteristics of stems/branches:

*Length*.—About 10 cm.

*Form*.—Round in cross section.

*Diameter*.—Approximately 1.0 cm.

*Color*.—Near RHS Greyed-Red 182A.

*Texture*.—Mainly glabrous. Very sparse, irregular hirsute hairs, 4 to 5 mm long colored near Greyed-Red 182D.

*Strength*.—Weak to moderate.

FOLIAGE

Arrangement: Emerging basally, with maturity 2 emerging from a branch split.

Quantity: Approximately 25 on a plant of this age.

Average length: Average range 18 to 22 cm.

Average width: Average range 18 to 20 cm.

Shape of blade: Very broad kidney shaped.

Apex: Elongated acute.

Base: Cordate. Non-overlapping.

Margin: Overall double serrate. 5 to 7 shallow angular lobes with deeper, irregular dentations. The entire margin is covered in very shallow crenation.

Texture of top surface: Glabrous, leathery. Rugose and puckered.

Texture of bottom surface: Glabrous. Very sparse hirsute hairs along main veins. Rugose and puckered.

Aspect: Puckered, overall flat.

Color:

*Young foliage upper side*.—Near RHS Greyed-Purple N187A. 189C. Densely speckled N187C throughout surface between veins. Speckles irregular rounds and ovals, 2 to 4 mm long and 2 to 3 mm wide.

*Young foliage under side*.—Near RHS Purple N186C.

*Mature foliage upper side*.—Near RHS Greyed-Green 189A. Densely speckled Greyed-Green 191D throughout surface between veins. Speckles irregular rounds and ovals, 4 to 9 mm long and 3 to 7 mm wide. Thick coloration along main veins near Greyed-Green N189A.

*Mature foliage under side*.—Near RHS Greyed-Purple 187A.

Venation:

*Type*.—Palmate.

*Venation color upper side*.—Near RHS Greyed-Purple N186A.

*Venation color under side*.—Near RHS Greyed-Purple N186C.

Petiole:

*Length*.—Average range 10 to 20 cm.

*Diameter*.—8 to 9 mm.

*Color*.—Near RHS Greyed-Red 182B.

*Texture*.—Very sparse, irregular hirsute hairs, 3 mm long colored near Greyed-Red 182D.

Stipule description: 1 or 2 per node, non-fleshy, becoming completely dry and papery before leaves fully expand.

*Length*.—Approximately 3.5 cm.

*Diameter*.—Approximately 1.3 cm.

*Apex*.—Apiculate.

*Color*.—Begins near Greyed-Purple 183B, quickly drying and turning Grey-Brown N199B.

*Texture*.—Glabrous.

FLOWER

Flowering habit: Continuously flowering during Spring and Summer. Flowering begins in May, in the Gulf Coast of the US.

Inflorescence and flower type and habit: Single flowers arranged in axillary cymes. Cymes held slightly above or within foliage, approximately 2 to 4 flowers per cyme.

Cyme size:

*Diameter*.—Approximately 11 cm.

*Height*.—Approximately 6 cm.

Flower longevity on plant: About 7 days.

Persistent or self-cleaning: Self-Cleaning.

Bud:

*Shape*.—Ovate.

*Length*.—Approximately 2 cm, including bracts. Tepal bud alone about 1.4 cm.

*Diameter*.—Approximately 1.2 cm, including bracts. Tepal bud alone about 1.0 cm.

*Color*.—Tepal bud near RHS Red-Purple N57A 52B. Immature bracts around bud colored near Red-Purple 66A.

Flower size:

*Diameter*.—Approximately 3.8 cm.

*Depth*.—Approximately 3.5 cm, including protruding stamens.

Tepals:

*Quantity*.—5.

*Arrangement*.—Rotate. Slightly overlapping.

*Length*.—Approximately 1.7 cm.

*Width*.—Approximately 1.1 cm.

*Shape*.—Ovate.

*Apex*.—Obtuse.

*Base*.—Broad attenuate.

*Margin*.—Entire.

*Aspect*.—Strong upward curve.
*Texture, upper and lower surfaces*.—Matte.
*Appearance, upper and lower surfaces*.—Slightly iridescent.
*Color*.—When opening, upper surface: Near RHS Red 55B. When opening, lower surface: Near RHS Red 55B, center vein 55A. Fully opened, upper surface: Near RHS Red 56B streaked 55C. Fully opened, lower surface: Near RHS Red 56D center vein 55A.

Flower bracts:
*Quantity per flower*.—2.
*Shape*.—Ovate, strongly concave.
*Length*.—Approximately 3.0 cm.
*Diameter*.—Approximately 1.8 cm, when manually flattened.
*Apex*.—Acute.
*Base*.—Truncate.
*Margin*.—Entire.
*Texture*.—Glabrous.
*Aspect*.—Strongly curved inward towards tepals.
*Color*.—Near RHS Red 51A when mature. Immature bracts near Red 49A.

Peduncles:
*Length*.—Average 3.5 cm.
*Diameter*.—Approximately 6 mm.
*Angle*.—About 15° to the lateral branch.
*Strength*.—Moderate, flexible.
*Texture*.—Glabrous.
*Color*.—Near RHS Red 50D thickly flushed 53B.

Pedicels:
*Length*.—Approximately 1.8 cm.
*Diameter*.—Approximately 3 mm.
*Angle*.—About 45° to the lateral branch.
*Strength*.—Moderate, flexible.
*Texture*.—Glabrous.
*Color*.—Near RHS Red-Purple 58D.

Fragrance: None.

REPRODUCTIVE ORGANS

Stamens:
*Number*.—8, arising from staminoidal column.

Anthers:
*Description*.—Fleshy, curly.
*Length*.—Free portion about 5 mm.
*Color*.—Near RHS Yellow 6C.
*Pollen*.—Not observed.

Pistil:
*Number*.—1.
*Length*.—Approximately 1.4 cm.
*Style*.—Length: Approximately 2 mm. Color: Near RHS Yellow 4B.
*Stigma*.—Shape: Linear. Color: Near RHS Yellow-Green 145D. Ovary Color: Near RHS Yellow-Green 145B.

OTHER CHARACTERISTICS

Seeds: Not observed.

Disease/pest resistance: Moderate resistance and susceptibility to common diseases and pests of *Begonia* have been observed in the new cultivar. Typical diseases found in hybrid *Begonias* include *Pythium* spp., *Rhizoctonia* spp., *Xanthomonoas campestris* and *Botrytis cineraria*. Insect pests include *Bemisia* spp., *Pseudococcidae* spp. and various *Coccoidea* spp.

Temperature tolerance: USDA Zone 7-9.

What is claimed is:

1. A new and distinct cultivar of *Begonia* plant named 'Neon Moon' as herein illustrated and described.

* * * * *